United States Patent [19]

Landes

[11] Patent Number: 4,626,501
[45] Date of Patent: Dec. 2, 1986

[54] LABELED DNA

[75] Inventor: Greg M. Landes, Northboro, Mass.

[73] Assignee: Integrated Genetics, Inc., Framingham, Mass.

[21] Appl. No.: 529,044

[22] Filed: Sep. 2, 1983

[51] Int. Cl.[4] .................... C12Q 1/68; C07H 17/00; C07H 19/00; C07D 473/00
[52] U.S. Cl. .......................... 435/6; 536/23; 536/26; 544/264; 544/269; 544/272; 935/77; 935/78
[58] Field of Search .............. 536/23, 26; 424/251, 424/253; 544/264, 269, 272, 280, 281; 435/6; 436/504, 508, 518, 528, 800, 804, 823; 935/77, 78

[56] References Cited

U.S. PATENT DOCUMENTS

| | | | |
|---|---|---|---|
| 4,139,346 | 2/1979 | Rabbani | 422/56 |
| 4,228,237 | 10/1980 | Hevey et al. | 435/7 |
| 4,282,287 | 8/1981 | Giese | 428/407 |
| 4,286,964 | 9/1981 | Seed | 424/1.1 |
| 4,358,535 | 11/1982 | Falkow et al. | 435/5 |

FOREIGN PATENT DOCUMENTS 2019408  4/1979  United Kingdom ............. 436/504

OTHER PUBLICATIONS

Fink et al. (1980) Analytical Biochemistry 108, 394–401.
Grunstein et al. (1975) Proc. Nat. Acad. Sci. USA 72(10), 3961–5.
Hsu et al. (1981) Jour. Histochem. and Cytochem. 29(4), 577–580.
Manning et al. (1975) Chromosoma 53, 107–117.
Sodja et al. (1977) Nucleic Acids Research, pp. 385–401.
Broker et al. (1977) Nucleic Acids Research, pp. 363–384.
Langer et al. (1981) Proc. Natl. Acad Sci USA 78(11), 6633–6637.
Langer-Safer et al. (1982) Proc. Natl. Acad. Sci. USA 79, 4381–5.
Renz (1983) BMBO Journal 2(6), 817–822.

Primary Examiner—Christine M. Nucker

[57] ABSTRACT

Polymeric, single-stranded DNA molecule which is labeled with a plurality of labels, the labels being bonded, via linking groups, to adenine and cytosine bases of the DNA molecule in substantially equal numbers, the labels being bonded to essentially none of the guanine or thymine bases of the DNA molecule, the DNA molecule being adapted for use as a probe in a nucleic acid hybridization assay.

24 Claims, 4 Drawing Figures

C = CYTOSINE

A = ADENINE

L = BSPSE LINKER

P = MICROPEROXIDASE

S = CHEMILUMINESCENT SUBSTRATE FOR MICROPEROXIDASE (LUMINOL)

LABELED DNA

BACKGROUND OF THE INVENTION

This invention relates to nucleic acid hybridization assays.

Such assays are well-known, and are becoming increasingly important in the diagnosis of a wide variety of medical disorders. Typically, a labeled, single-stranded DNA probe which is at least partly homologous with the DNA or RNA of interest is reacted with the denatured nucleic acid of a sample suspected of containing the DNA or RNA of interest. Labeled hybrid complexes indicate the presence of such DNA or RNA.

Probes can be labeled in any of a variety of ways. Some labeling methods are direct, i.e., the label, which is bonded to the probe is itself detectable; examples are radioactive isotopes. Other labels are indirect, i.e., the label is not itself detectable until it undergoes one or more reactions following hybridization; an example is a compound such as biotin, a label which is not itself detectable, but becomes detectable after it reacts with avidin bound to a detectable chemical entity such as a fluorophore.

For convenience, the term "label", as used herein, refers to directly detectable entities such as radioactive isotopes, as well as to indirectly detectable entities such as biotin. The entity, e.g., avidin, to which an indirectly detectable entity bonds to become detectable, is referred to herein as an "indicator".

SUMMARY OF THE INVENTION

In general, the invention features a polymeric, single-stranded DNA molecule which is labeled with a plurality of labels, the labels being bonded, via linking groups, to adenine and cytosine bases of the DNA molecule in substantially equal numbers (within 5%), the labels being bonded to essentially none (less than 0.5%) of the guanine or thymine bases of the DNA molecule, the DNA molecule being adapted for use as a probe in a nucleic acid hybridization assay. Preferably at least half of the adenine and cytosine bases are labeled.

The DNA molecules of the invention are preferably made by reacting a polymeric DNA molecule with a heterofunctional reagent of the formula

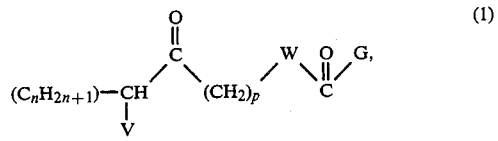

wherein n is between 0 and 10, inclusive; p is between 1 and 10, inclusive, preferably between 1 and 4, inclusive; V is a halogen; W is nothing or $SO_2$—$(CH_2)_q$, wherein q is between 1 and 10, inclusive, preferably between 1 and 4, inclusive; and G is either a label X, or the reactive group OR, wherein R is one of: (1) an alkyl group, preferably having five or fewer carbon atoms, most preferably three or fewer carbon atoms (e.g. ethyl); (2) a heteroalkyl group, preferably having five or fewer carbon atoms and containing only the elements oxygen, nitrogen, and carbon (e.g., N-hydroxysuccinimidyl); (3) an aryl group, preferably having twelve or fewer carbon atoms (e.g., phenyl); (4) an aralkyl group, preferably having fifteen or fewer carbon atoms (e.g., ethylphenyl); (5) a heteroaryl group, preferably having fifteen or fewer carbon atoms and containing only the elements oxygen, nitrogen, hydrogen, and carbon (e.g., p-nitrophenol); or (6) a hydrogen atom.

The above reaction produces a polymeric DNA molecule in which at least some of the adenine and cytosine bases are derivatized to their respective etheno analogs, of the formula

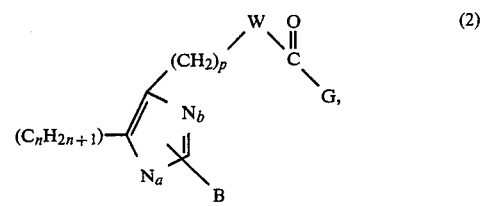

wherein n is between 0 and 10, inclusive, preferably between 0 and 3, inclusive; p is between 1 and 10, inclusive, preferably between 1 and 4, inclusive; $N_a$ is N-1 of adenine or N-3 of cytosine; $N_b$ is N-6 of adenine or N-4 of cytosine; B is the remainder of the adenine or cytosine base; and W and G are as defined above for formula (1).

When G in formula (2), above, is OR, the DNA molecule can be further derivatized with a label, either directly or via a second linking group, to give a formula (2) compound in which G is X, X having replaced OR.

In formula (2), n is most preferably 0, p is most preferably 2, and W is most preferably $SO_2$—$(CH_2)_q$, q most preferably being 2.

Label X includes a detectable entity, designated "Z" herein, which can be, e.g., an enzyme, catalyst, hapten, one of a specific binding pair, e.g. an immunological pair (e.g., antigen/antibody or biotin/avidin), or a spectrophotometrically, radioactively, or fluorescently detectable molecule or atom. In the case of specific binding pairs such as biotin/avidin, the second member of the pair, e.g. avidin, is bonded to a detectable chemical entity such as a fluorophore, or an enzyme such as horseradish peroxidase (HRP). In the case of HRP, detection is accomplished via a substrate for HRP; a preferred such substrate is the chromogen diaminobenzidine. Z can be any detectable entity, the chemical composition of Z not being critical.

As mentioned above, the label can be bonded directly to the acyl carbon atom; i.e., X can consist only of the detectable entity Z and no additional linking group.

Alternatively, X can include both the detectable entity Z and a second linking group. One such X has the formula:

where $1 \leq r \leq 10$, preferably $4 \leq r \leq 8$, and most preferably $r = 6$.

Generally, if a second linking group is present, derivatization with that group will precede the attachment of Z; i.e. the second linking group, which includes a reaction site for Z, is reacted with the etheno analog of formula (2), to form:

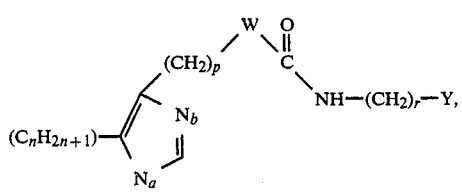

(4)

wherein Y is a reactive site, e.g. $NH_2$, COOH, or SH, to be replaced by Z, and n, p, W, $N_a$, and $N_b$ are as defined for formula (2).

The DNA molecule can, as described above, comprise a fragment in which bases which form part of the hybridizing fragment itself are labeled with detectors. Alternatively, the DNA molecules can comprise two portions, a first portion which is substantially unlabeled and which is capable of specifically binding to the specific nucleic acid sequence of interest, and a homo- or heteropolymeric tail portion which is labeled as described above.

The DNA molecules of the invention offer a number of advantages. Easy to handle non-isotopic labels such as catalytic labels are readily attached to the molecules and, furthermore, can be attached in numbers approaching half of the total number of bases (since half the bases are adenine and cytosine) or, if a homopolymeric tail is used, close to all of the bases in the tail, providing amplification and concomitant sensitivity. In the tail embodiment, only the tail is labeled, so that label will not interfere with the hybridization process.

Other features and advantages of the invention will be apparent from the following description of the preferred embodiments thereof, and from the claims.

DESCRIPTION OF THE PREFERRED EMBODIMENTS

Figure 1:
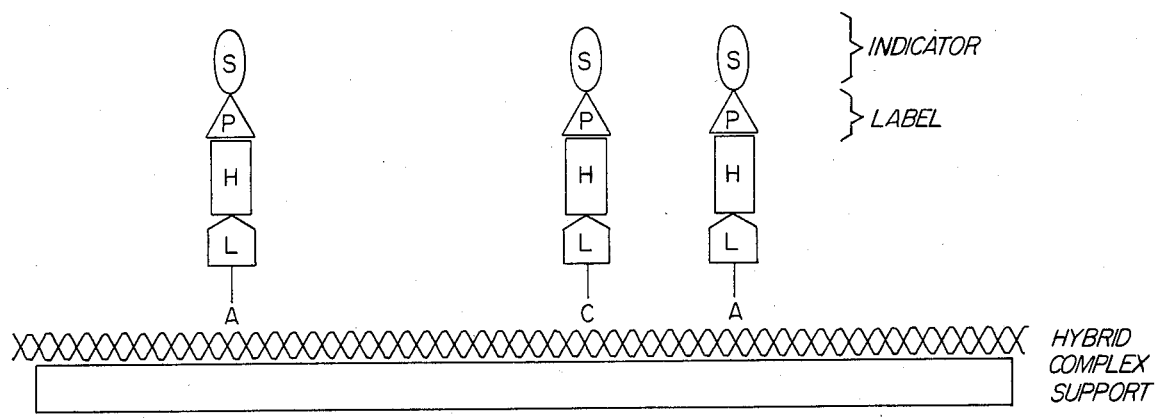

We first briefly describe the drawings, and then describe the general chemistry involved in preparing a non-isotopic DNA probe. We then present specific examples, and finally describe the use of such probes in hybridization assays, and the respective methods of detecting the resulting hybrids.

DRAWING

FIGS. 1–4 are diagrammatic representations of the operation of preferred embodiments of the invention.

STRUCTURE

The DNA probes have the structure described in the Summary of the Invention above.

SYNTHESIS

Generally the starting DNA molecule is single-stranded DNA probe and capable of specifically hybridizing to a specific nucleotide (RNA or DNA) sequence; such probes are obtained or made using conventional, well-known techniques. One example of a useful group of probes are the Salmonella-specific DNA probes described in Taber et al. U.S. Pat. Appln. entitled "Test for Salmonella in Food", filed on the same day as this application, assigned to the same assignee as this application, hereby incorporated by reference.

The derivatization of at least some of the adenines and cytosines of the single-stranded DNA probe (either the hybridizing portion of the probe or the homopolymeric synthetic tail) is carried out, using the heterofunctional cross-linker

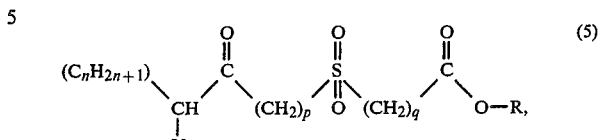

(5)

wherein V, n, p, q, and R are as defined above. The cross linker of formula (5) is made by the procedure of Fink et al. (1980) Anal. Biochem. 108, 394–401.

In formula (5), above, W is $SO_2$—$(CH_2)_q$. If, alternatively, W is nothing, i.e., $(CH_2)_p$ is bonded directly to

the cross linker is made by appropriately modifying the Fink et al. reaction, as follows. Equimolar amounts of the desired keto-acid or keto-ester are mixed with molecular halogen $V_2$ (usually bromine) in chloroform. After consumption of the halogen, the $\alpha$-haloketo-acid or ester may be used without purification, or may be further purified, using standard techniques.

Generally, the reaction between the cross-linker and the DNA is carried out for about 1 hour at about 37° C., and excess cross-linker is removed, e.g. by organic extraction.

Adenine and cytosine react with the cross-linker to form, after dehydration, a stable derivative. The alkylation reaction is illustrated below, in which adenine is shown reacting with the linker 3-(4-bromo 3-oxobutane 1-sulfonyl)-propionate N-hydroxy succinimide ("BSPSE"); i.e., in formula (5), n is 0, p is 2, q is 2, V is bromide, and OR is N-hydroxysuccinimidyl:

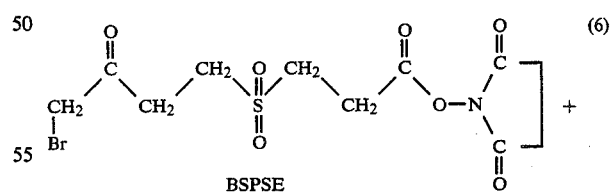

BSPSE (6)

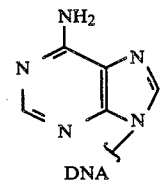

DNA

↓

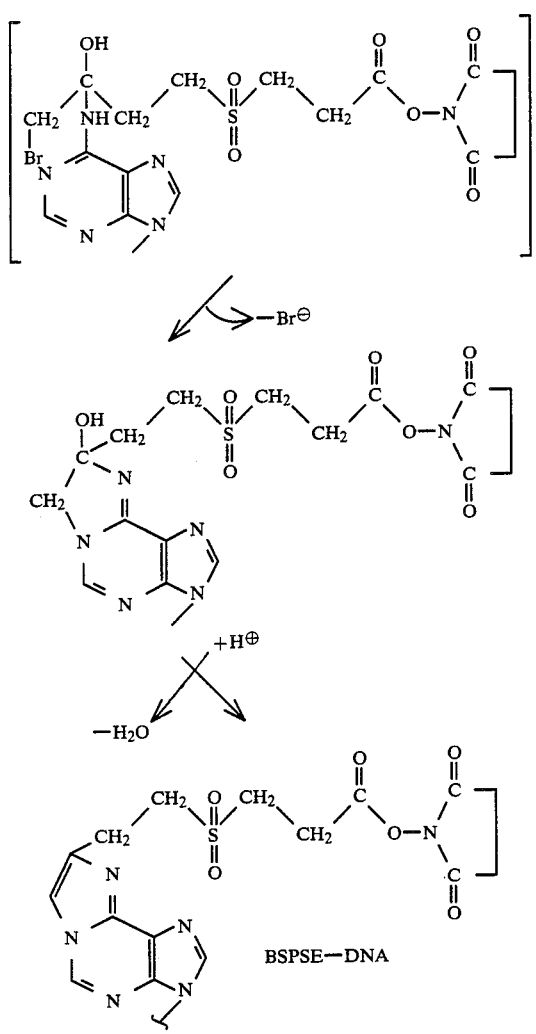

The resulting derivatized DNA molecule, containing a highly reactive ester group, is the precursor to a wide variety of labeled DNA molecules. Primary amines, present on antigens, enzymes, haptens, or substituted aliphatics, can react with the acyl carbon atom of the ester group to form an amide bond. Alternatively, additional linking functionalities can be bonded to the first linking group; e.g. diaminoalkanes, amino acids, or aminoalkylthiols can react with the ester group to generate an amide bearing, respectively, an amine, carboxylic acid, or thiol available for derivatization with a label.

Frequently the attachment of an additional linking functionality is carried out at pH 7 to 8 in buffer, e.g. $NaHCO_3$. The reactants are incubated together for an amount of time sufficient to allow the reaction to proceed to completion, e.g., 4–20 hours, at a suitable temperature, e.g., room temperature. The final product is purified, e.g. by gel filtration.

Detailed descriptions of the formation of non-isotopically labeled hybridization probes are given below.

EXAMPLE 1

Horseradish Peroxidase-Labeled DNA Probes

The enzymatic label horseradish peroxidase (HRP) is attached to a DNA probe via the linking groups BSPSE and 1,6-hexane diamine (HDA), as follows.

Eight parts of the desired single-stranded DNA at a concentration of 1.25 mg/ml in distilled water are mixed with one part 1M NaOAc, pH 6. The solution of DNA and NaOAc are pre-warmed to 37° C. and then one part of 100 mM BSPSE in DMSO is added to the mixture. The final concentration of reagents is 1 mg/ml single-stranded DNA, 100 mM NaOAc, pH 6, 10 mM BSPSE and 10% (v/v) DMSO. The solution is incubated for 1 hour at 37° C. and then extracted 3 times with chloroform to remove unreacted BSPSE.

The resulting BSPSE-modified DNA next is incubated with hexane diamine-treated HRP. Treatment of HRP with 1,6-hexane diamine (HDA) allows efficient coupling of HRP to BSPSE-modified DNA. HDA treatment involves mixing together the following components:

4 parts of 4 mg/ml HRP (Sigma Chemical Company, St. Louis, MO., Type VI) in distilled water;

1 part 100 mM $NaIO_4$ (same supplier as for HRP)

The mixture is incubated at room temperature for 20 minutes. The oxidation reaction is then quenched by adding either glucose or ethylene glycol to 100 mM of the mixture. The low molecular weight redox products are then eliminated by dialysis against 1 mM NaOAc, pH 4, or by G-25 Sephadex column chromatography in 1 mM NaOAc, pH 4.

8 parts of the resulting periodate-oxidized HRP are mixed with 1 part fresh 1M $NaHCO_3$, and 1 part of 10% (v/v) HDA, pH 9.5 with HCl. The mixture is incubated at room temperature for more than 4 hours. Unreacted HDA is removed by dialysis against 0.1M $NaHCO_3$ at 4° degrees C. HDA-modified HRP is stored at 4 degrees C. until use.

The derivatized DNA is then labeled with HRP by mixing the following:

2 parts BSPSE-modified DNA (200 ug),
4 parts distilled water,
1 part fresh 1M $NaHCO_3$,
3 parts HDA-treated periodate-oxidized HRP (about 600–900 ug HRP)

The mixture is incubated overnight at room temperature.

Free and bound HDA-treated HRP are separated by Bio-Gel A0.5M or A5M column chromatography in 50 mM $Na_2B_4O_7$, pH 8, 100 mM NaCl. The excluded fractions are recovered and pooled. The absorbance of the pooled material is measured at both 403 and 260 nm. The extent of modification is determined based on a molar extinction coefficient of HRP of 10,200 at 403 nm and of dNMP of 6,500 at 260 nm.

The above steps are illustrated by the following reaction diagram:

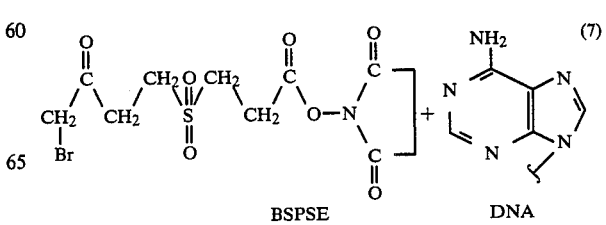

BSPSE          DNA          (7)

-continued

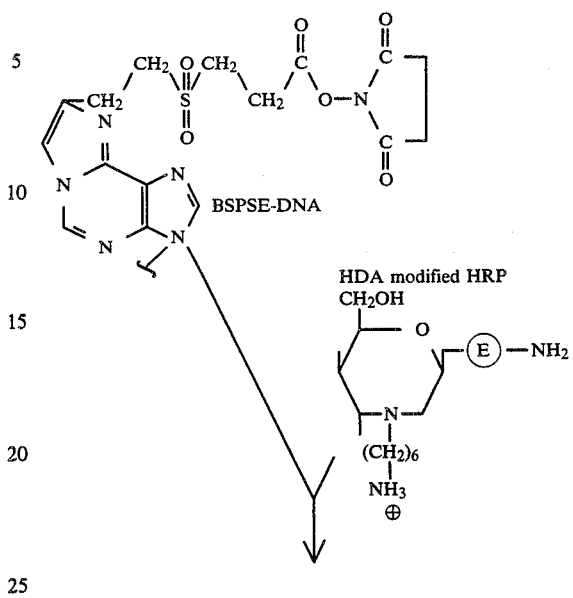

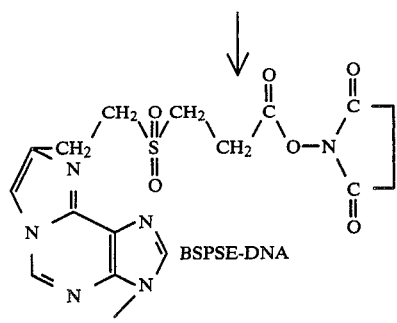

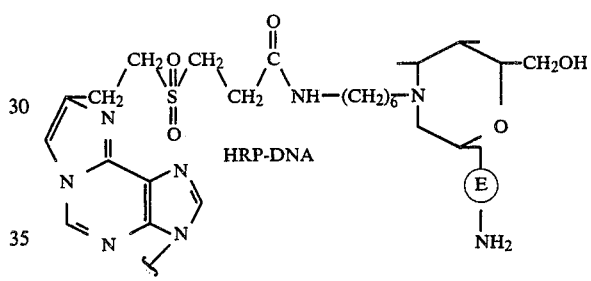

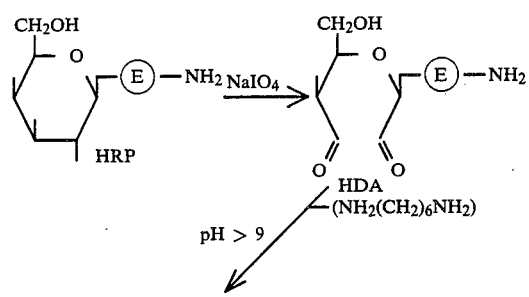

EXAMPLE 2

Dinitrophenyl-Labeled DNA Probes

The haptenic label dinitrophenyl (DNP) is attached to a DNA probe via the linking group BSPSE as follows.

First, BSPSE-derivatized DNA is prepared, as described above. To 5 parts of BSPSE-derivatized DNA are added 1 part fresh 1M NaHCO$_3$ and 12 parts 11.3 mM N-ε-Dinitrophenyl-L-lysine-HCl in 200 mM NaHCO$_3$. The mixture is incubated overnight and then dialysed against 0.1M NaHCO$_3$. The absorbance of the product is measured at both 360 mn and at 260 mn. The extent of derivatization is determined based on a molar extinction coefficient of DNP of 16,000 at 360 nm and of dNMP of 6500 at 260 nm.

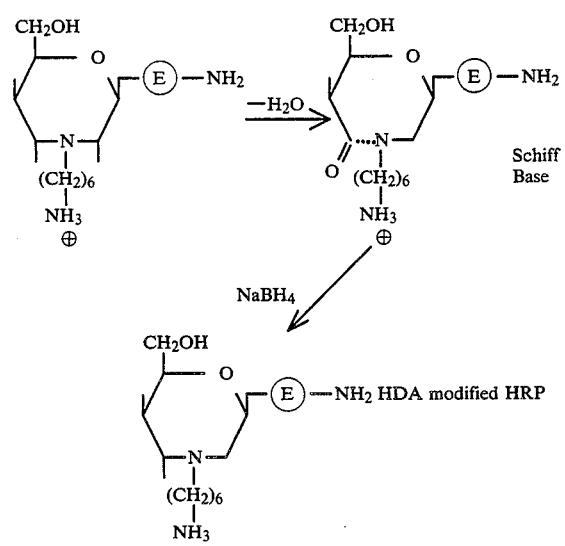

The above steps are illustrated by the following reaction diagram:

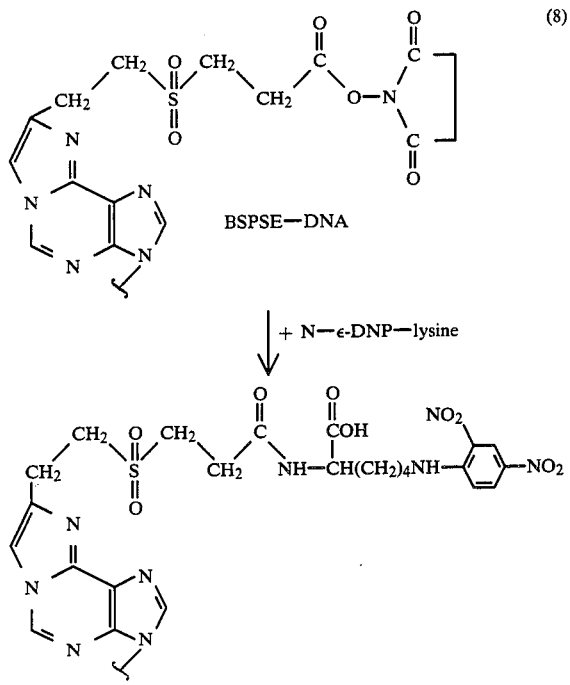

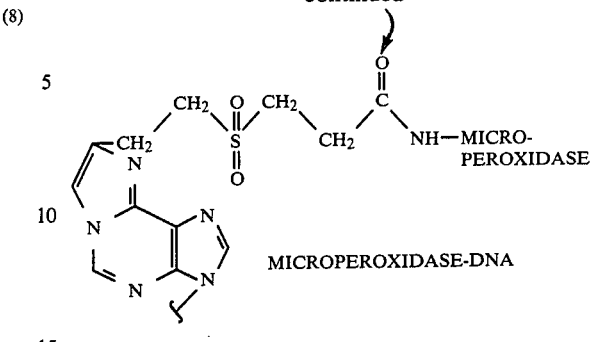

EXAMPLE 4

Biotinylated DNA Probes

The indirect label biotin is attached to a DNA probe via the linking groups BSPSE and HDA, as follows:

First, BSPSE-derivatized DNA is prepared, as described above. Eight parts of BSPSE-derivatized DNA are mixed with 1 part 10% (v/v) HDA, pH 7.8 and 1 part 1M NaHCO$_3$. The mixture is incubated for at least 4 hours at room temperature and then unreacted HDA is removed by dialysis against 0.1M NaHCO$_3$.

The resulting product is linked to biotin by mixing 8 parts by HDA-treated BSPSE-DNA with 1 part 40 mM N-Hydroxysuccinimidobiotin (in dimethylformamide) and 1 part 1M NaHCO$_3$. After incubating for more than 4 hours, unreacted biotin is eliminated by dialysis against 0.1M NaHCO$_3$.

The above steps are illustrated by the following reaction diagram:

EXAMPLE 3

Microperoxidase-Labeled DNA Probes

The enzymatic label microperoxidase is attached to a DNA probe via the linking groups BSPSE and HDA, as follows:

First, BSPSE-derivatized DNA is prepared, as described above. Three parts of the BSPSE-DNA are mixed with one part 1M NaHCO$_3$ and 5 parts of 20 mg/ml microperoxidase (Sigma Chemical Company at Louis, MO). The mixture is incubated overnight and then purified by column chromatography on Bio-Gel A0.5M. The excluded column fractions are pooled and the absorbance is measured at both 260 and 403 nm. The extent of modification is measured using the same extinction coefficients as used for HRP-DNA.

The above steps are illustrated by the following reaction diagram:

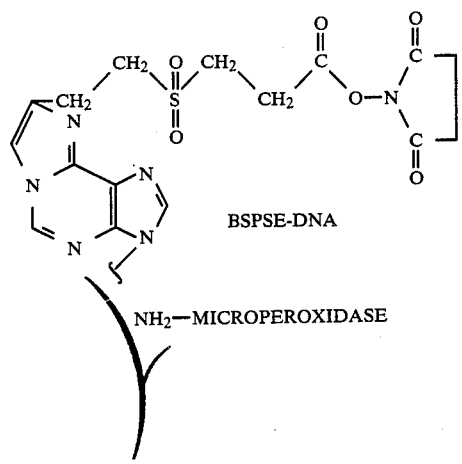

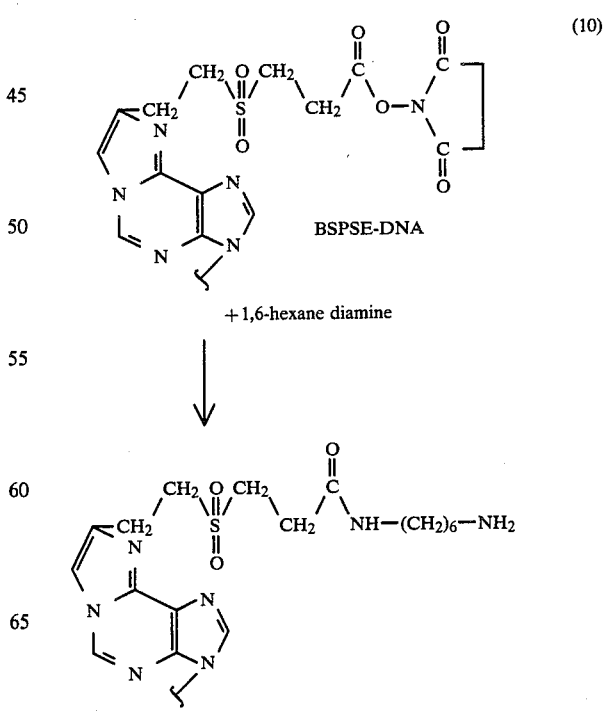

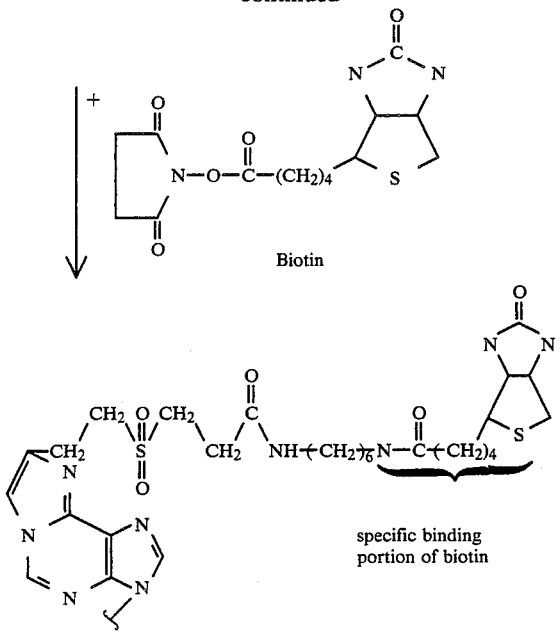

Biotin specific binding portion of biotin

STRUCTURAL PERMUTATIONS

If a homopolymeric tailed probe is used, the polyadenine or polycytosine tail can be first labeled, as above, and then attached to the hybridizing portion of the DNA probe, so that only the tail is labeled. Alternatively, the tail can first be enzymatically attached to double stranded DNA, using conventional techniques, and then, because the double stranded DNA is non-reactive, the tailed double stranded DNA can be alkylated and labeled, as above, resulting in labeling only of the reactive tail.

USE

The DNA probes of the invention can be used in any test or assay in which the nucleic acid sequence to which they specifically hybridize is to be detected or quantified. Any conventional hybridization techniques can be used, e.g. those described in Grunstein et al. (1975) PNAS USA 72, 3961 and Falkow et al. U.S. Pat. No. 4,358,535, hereby incorporated by reference. A specific example of a non-isotopic hybridization assay employing any of the DNA probes described above is as follows.

The double-stranded DNA or bacterial cell culture to be assayed is applied and fixed to a solid support (e.g., nitrocellulose, mixed cellulose esters, or nylon) by spotting 1-5 ul of a sample onto the filter, allowing the filter to air dry, and then placing the filter on a square of Whatman 3MM paper saturated with 0.5N NaOH, 1.5M NaCl. After 5-15 minutes, the membrane filter is transferred to a square of Whatman 3MM saturated with 3M NaCl, 1.5M Tris, pH 7.5. After neutralization, the membrane containing the sample is immersed in absolute ethanol and then allowed to dry, to permanently fix the DNA to the solid support.

The membrane is pre-hybridized at 37° C. in pre-hybridization buffer which consists of the following components: 45% formamide, 25 mM NaPO$_4$, pH 6.8, 5X Denhardt's Solution (1X is 0.02% (w/v) of each of bovine serum albumin, polyvinylpyrrolidone, and Ficoll 500), 250 ug/ml sonicated, denatured salmon sperm or calf thymus DNA. After 30 minutes the pre-hybridization solution is replaced with hybridization buffer containing 0.1–10 ug/ml of non-isotopic hybridization probe. The hybridization cocktail is chemically equivalent to the pre-hybridization cocktail except that it also contains 10% (w/v) dextran sulfate and the non-isotopic hybridization probe. The hybridization reaction is allowed to proceed for 2 hours at 37° C.

Non-hybridized probe is removed by repetitive washes of the solid support with an established wash regimen, e.g., 3 washes of 10 minutes each with 10 mM NaCl at 37° C.

Generally, after hybridization is carried out and hybrid complexes are formed, the label is detected or measured, using a technique appropriate for the particular label employed. If the label is detectable without being complexed to an indicator, hybrid complexes are simply detected using an appropriate means, e.g. by detecting fluorescence, light emission, radioactivity, or electron density. If the label must be complexed with an additional chemical entity, i.e. an indicator, before detection is possible, then the step of contacting hybrid complexes with the indicator is carried out and the resultant label/indicator complexes detected or measured. For example, if the label is one of a specific binding pair, e.g. the antigen of an immunological pair, the hybrid complex is contacted with the antibody of the pair, and immune complexes are then detected. To facilitate detection, the second of the specific binding pair (i.e. the indicator) can have attached to it a detectable entity, e.g. an enzyme, fluorescent compound, etc.

Specific examples of the methods employed for the detection of the labeled probes described above are as follows.

EXAMPLE 5

Detection of HRP-Labeled DNA Probes

Referring to FIG. 1, to detect hybrid complexes labeled with HRP, the solid support is overlayed with any one of many chromogenic HRP substrates, e.g., 2,2'azino-di-(3-ethyl-benzthiazoline sulfonate) (ABTS), 3,3'-diaminobenzidine (DAB), or 3,3',5,5'-tetramethylbenzidine. In the case of the substrate ABTS, the substrate solution, consisting of 2 mM ABTS, 2.5 mM H$_2$O$_2$ in 100 mM NaOAc, 50 mM NPO$_4$, pH 4.2, is added to the support and the reaction is allowed to proceed for approximately 10–30 minutes, after which time green colored dots will have formed for samples containing sequences complementary to the HRP-labeled DNA probe. The extent of hybridization can be quantitated by measuring the absorbance of the recovered substrate solution. As is illustrated in FIG. 1, only the cytosine and adenine bases of the DNA probe are labeled with HRP.

Since oxidized ABTS is soluble, a more permanent record of the hybridization reaction can be obtained if a peroxidase substrate is used which generates an insoluble product upon oxidation. The benzidine substrates listed above satisfy this requirement. For example, 0.05% DAB, 0.02% H$_2$O$_2$, 0.02% CoCl$_2$ in 10 mM Tris, pH 7.5 yields a convenient substrate solution which produces a purplish precipitate at the site of hybridization.

EXAMPLE 6

Detection of DNP-labeled DNA Probes

Figure 2:
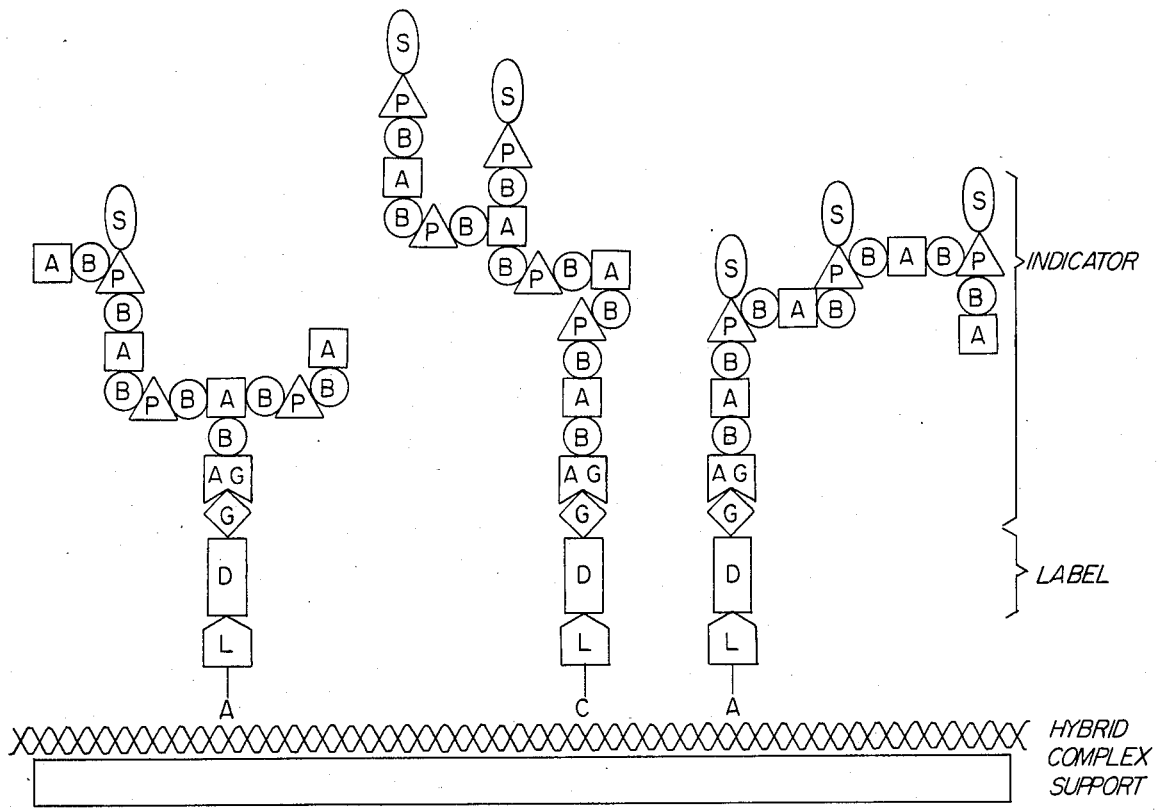

Referring to FIG. 2, to detect hybrid complexes labeled with DNP, which is not itself detectable, the DNP is reacted with a detectable indicator to which it selectively (i.e., preferentially) binds. In the example illustrated in FIG. 2, the indicator consists of the following: goat anti-DNP antibody, which selectively binds to the DNP-labeled hybrid complexes; biotinylated anti-goat antibody; biotin; avidin; HRP; and a substrate for HRP. In the illustrated example, the reactions involving the antibodies and biotin are followed by the ABC HRP detection method of Hsu et al. (1981) J. Histochem. and Cytochem. 29, 577–580.

Alternatively, an HRP-labeled anti-DNP antibody could be used to detect DNP-labeled complexes. Another alternative would be to use a double antibody system employing an enzyme rather than biotin.

EXAMPLE 7

Detection of Microperoxidase-Labeled DNA Probes

Figure 3:
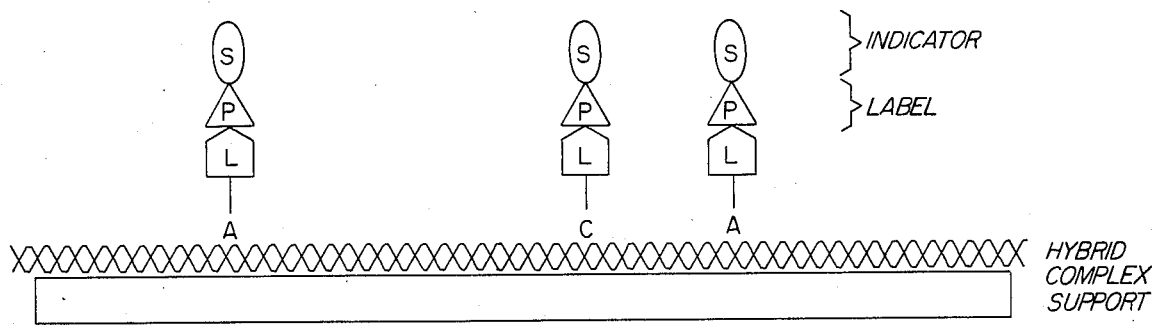

Referring to FIG. 3, to detect hybrid complexes labeled with microperoxidase, a chemiluminescent substrate, luminol, for microperoxidase is used. The solid support bearing the labeled hybrid complexes is placed in a borosilicate test tube to which is added luminol, NaOH, and hydrogen peroxide. The contents are mixed and then placed in a fluorometer with the incident light source off and the photomultiplier on. The amplitude of the signal is compared to that of known quantities of microperoxidase-labeled probe.

Alternatively, the hybridized material can first be removed from the solid support using NaOH and then the other reagents added to the reaction, and the chemiluminescent activity measured as described above.

EXAMPLE 8

Detection of Biotin-Labeled DNA Probes

Figure 4:
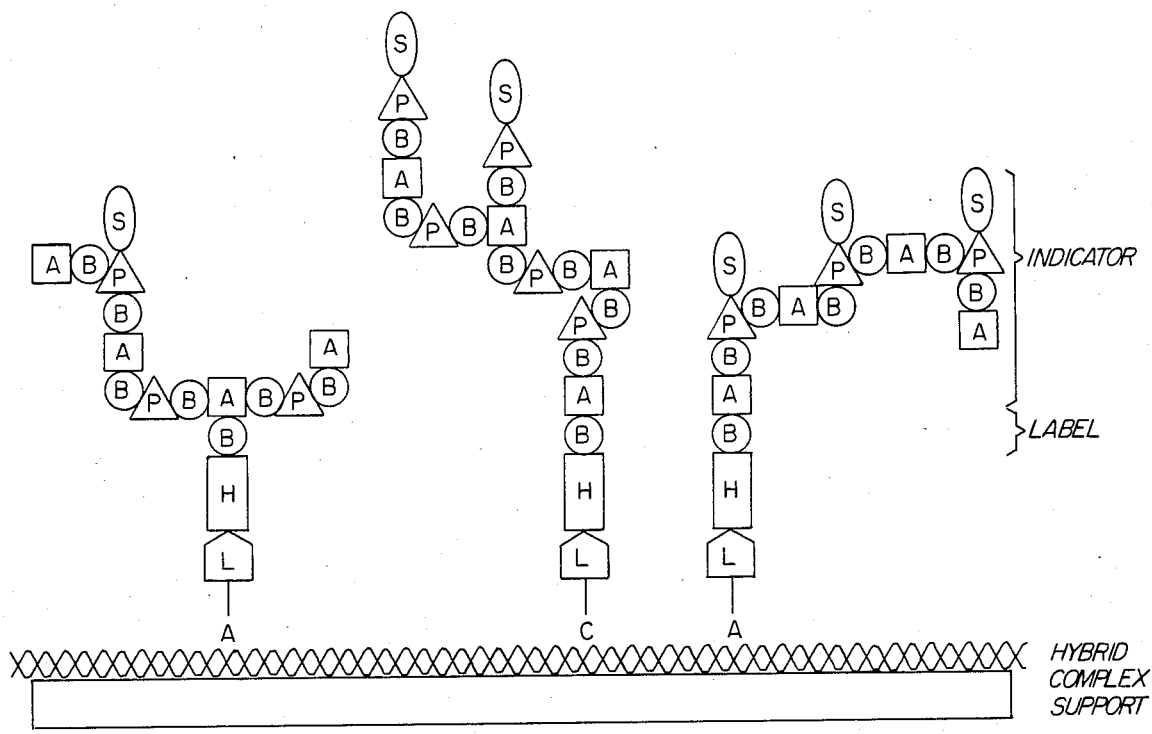

Referring to FIG. 4, to detect biotin-labeled hybrid complexes, avidin, HRP, and a substrate for HRP are used. The method is essentially that described in Hsu et al, id.

OTHER EMBODIMENTS

Other embodiments are within the following claims. For example, as has been mentioned, a wide variety of labeling systems can be used with the invention. The enzyme alkaline phosphatase, for example, can be used in place of HRP, and detected by the color change produced when contacted with the substrate 6 mM p-nitrophenylphosphate in 1 mM 2n $Cl_2$, 1 mM $MgCl_2$, 100 mM glycine (pH 10.4).

In the above examples, the DNA is derivatized with BSPSE prior to attachment of label. Alternatively, the BSPSE can be reacted with the label prior to the derivatization of the DNA.

What is claimed is:

1. A polymeric DNA molecule wherein at least some of the adenine and cytosine bases of said DNA molecule are derivatized to their respective etheno analogs, said analogs having the formula

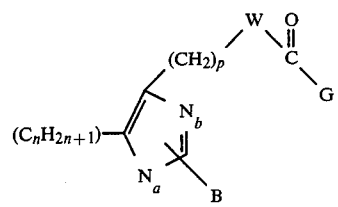

wherein n is between 0 and 10, inclusive; each p is between 1 and 10, inclusive; $N_a$ is N-1 of adenine or N-3 of cytosine; $N_b$ is N-6 of adenine or N-4 of cytosine; B is the remainder of the adenine or cytosine base; W is $SO_2$—$(CH_2)_q$, q being between 1 and 10, inclusive; and G is X, X being NH—$(CH_2)_r$—Z wherein $1 \leq r \leq 10$, Z being a detectable entity.

2. The DNA molecule of claim 1 wherein n is 0, p is 2, and W is $SO_2$—$(CH_2)_q$, wherein q is 2.

3. The DNA molecule of claim 1 wherein at least half of the adenine bases and at least half of the cytosine bases of said DNA molecule are derivatized.

4. The DNA molecule of claim 1 wherein G is X, X comprising one of a specific binding pair.

5. The DNA molecule of claim 1 wherein G is X, X comprising a detectable enzyme.

6. The DNA molecule of claim 1 wherein G is X, X comprising a detectable hapten.

7. The DNA molecule of claim 1 wherein G is X, X comprising a radioactively detectable atom.

8. The DNA molecule of claim 1 wherein G is X, X comprising a spectro photometrically detectable molecule.

9. The DNA molecule of claim 1 wherein G is X, X comprising a fluorescent molecule.

10. The DNA molecule of claim 1 wherein Z is biotin or an avidin-specific binding derivative thereof.

11. The DNA molecule of claim 10 wherein said specific binding derivative of biotin is

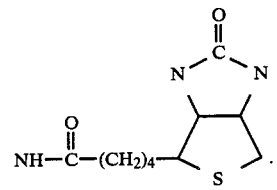

12. The DNA molecule of claim 4 wherein said one of a specific binding pair is one of a specific binding immunological pair.

13. The DNA molecule of claim 12 wherein said one of a specific binding immunological pair is one of an antibody/antigen pair.

14. The DNA molecule of claim 1 wherein Z is a fluorescent molecule.

15. The DNA molecule of claim 1 wherein Z is a spectro photometrically detectable molecule.

16. The DNA molecule of claim 1 wherein Z is a radioactively detectable atom.

17. The DNA molecule of claim 1 wherein said etheno analogs of said DNA molecule have the formula:

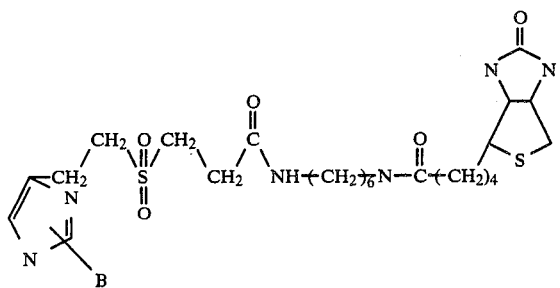

18. The DNA molecule of claim 1 wherein said etheno analogs of said DNA molecule have the formula:

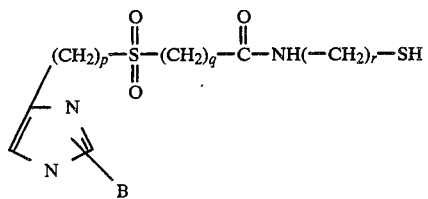

19. The DNA molecule of claim 1 wherein said etheno analogs of said DNA molecule have the formula:

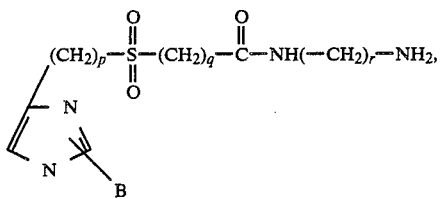

wherein r is between 1 and 10, inclusive.

20. The DNA molecule of claim 1 wherein said etheno analogs of said DNA molecule have the formula:

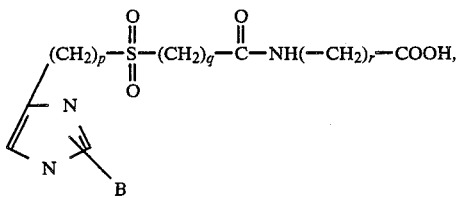

wherein r is between 1 and 10, inclusive.

21. A polymeric DNA molecule wherein at least some of the adenine and cytosine basis of said DNA molecule are derivatized to their respective etheno analogs having the formula:

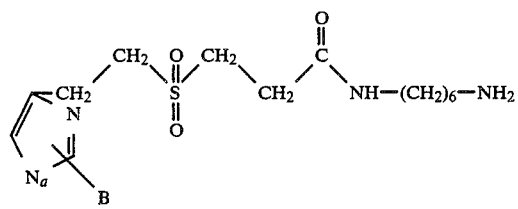

wherein $N_a$ is N-1 of adenine or N-3 of cytosine; $N_b$ is N-6 of adenine or N-4 of cytosine; and B is the remainder of said adenine or cytosine base.

22. A method of making a probe for use in a nucleic acid hybridization assay for a specific nucleic acid sequence, said method comprising providing a single-stranded polymeric DNA molecule capable of specifically hybridizing with said nucleic acid sequence, reacting said DNA molecule with a compound of the formula

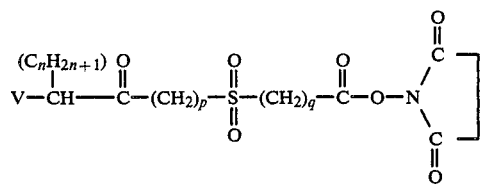

wherein V is a halogen; n is between 0 and 10, inclusive; and each p and q, independently, is between 1 and 10, inclusive, whereby at least some of the adenine and cytosine bases of said DNA molecule are derivatized to their respective etheno analogs, said analogs having the formula

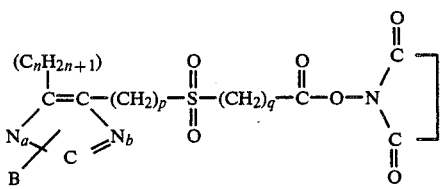

wherein n is between 0 and 10, inclusive; each p and q, independently, is between 1 and 10, inclusive; $N_a$ is N-1 of adenine or N-3 of cytosine; $N_b$ is N-6 of adenine or N-4 of cytosine; and B is the remainder of the adenine or cytosine base, performing one or more steps to substitute, for

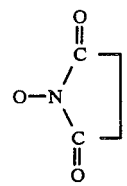

on said analogs, a substituent comprising a label which either is capable of being detected or is capable of selectively bonding to an indicator to form a detectable complex.

23. A polymeric, single-stranded DNA molecule adapted for use as a probe in a nucleic acid hybridization assay for a specific nucleic acid sequence, said molecule comprising a first portion capable of specifically hybridizing with said specific nucleic acid sequence, and a second tail portion not capable of so hybridizing, said tail portion being labeled with a plurality of labels and said first portion being substantially unlabeled wherein said tail contains adenine or cytosine bases, and is substantially free of guanine and thymine bases, and wherein at least some of said adenine or cytosine bases have bonded to them a substituent of the formula

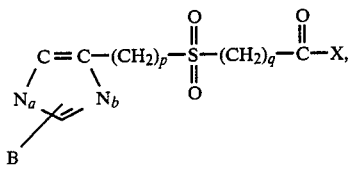

wherein n is between 0 and 10, inclusive; each p and q, independently, is between 1 and 10, inclusive; $N_a$ is N-1 of adenine or N-3 of cytosine; $N_b$ is N-6 of adenine or N-4 of cytosine; B is the remainder of the adenine or cytosine base; and X is NH—$(CH_2)_r$—Z, wherein $1 \leq r \leq 10$ and Z is a detectable chemical entity.

24. A method of making a probe for use in a nucleic acid hybridization assay for a specific nucleic acid sequence, said method comprising providing a single-stranded polymeric DNA molecule capable of specifically hybridizing with said nucleic acid sequence, reacting said DNA molecule with a compound of the formula

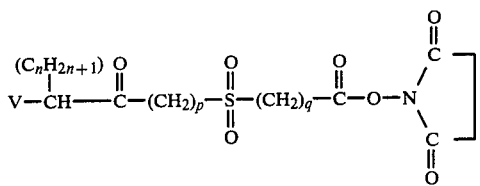

wherein V is a halogen; n is between 0 and 10, inclusive; and each p and q, independently, is between 1 and 10, inclusive, whereby at least some of the adenine and cytosine bases of said DNA molecule are derivatized to etheno analogs, performing one or more steps to substitute, for

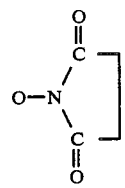

on said analogs, a substituent comprising a label which either is capable of being detected or is capable of selectively bonding to an indicator to form a detectable complex.

* * * * *

UNITED STATES PATENT AND TRADEMARK OFFICE
CERTIFICATE OF CORRECTION

PATENT NO. : 4,626,501
DATED : December 2, 1986
INVENTOR(S) : Greg M. Landes

It is certified that error appears in the above-identified patent and that said Letters Patent are hereby corrected as shown below:

In column 3, line 29, "concomitant" is misspelled. In the two formulae in column 5, between lines 5-30, and in the formula in column 7, between lines 10-20, replace that part of the formula shown as " 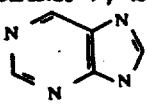 " with — 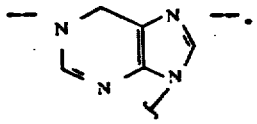 —.

In the formula in column 15, between lines 60-65 (claim 21), replace that part of the formula shown as " 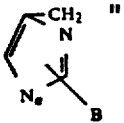 " with — 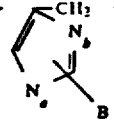 —.

Signed and Sealed this

Twenty-eighth Day of April, 1987

Attest:

DONALD J. QUIGG

Attesting Officer        Commissioner of Patents and Trademarks